United States Patent [19]

Kim

[11] Patent Number: 4,734,414
[45] Date of Patent: Mar. 29, 1988

[54] ANTI-INFLAMMATORY AND ANTI-ARTHRITIC PYRAZOLO-[1,5-A]-1,3,5-TRIAZINE DERIVATIVES, COMPOSITIONS, AND METHOD OF USE THEREFOR

[75] Inventor: Sun H. Kim, Chestnut Hill, Mass.

[73] Assignee: Biomeasure, Inc., Hopkinton, Mass.

[21] Appl. No.: 907,039

[22] Filed: Sep. 12, 1986

Related U.S. Application Data

[63] Continuation-in-part of Ser. No. 741,819, Jun. 6, 1985, abandoned.

[51] Int. Cl.[4] .................. A61K 31/38; A61K 31/44; A61K 31/53; C07D 251/72
[52] U.S. Cl. .......................... 514/245; 514/246; 544/211; 544/212; 544/219; 544/220
[58] Field of Search ............... 544/211, 212, 219, 220; 514/245, 246

[56] References Cited

PUBLICATIONS

Capuano et al, Chem. Ber. 104, (1971) 3039–3047.
Senga et al, J. Med. Chem., 25 (1982) pp. 243–248.
Durant et al, J. Med. Chem., 20 (1977) pp. 901–907.
Kobe et al, J. Het., 11 (1974) pp. 199–204.
Capuno et al. (1974) Chem. Ber. 104:3039.
Kobe et al. (1974) J. Het. Chem. 11:199.
Senga et al. (1973) J. Het. Chem. 12:893.
Senga et al. (1982) J. Med. Chem. 25:243.
Durant et al. (1977) J. Med. Chem. 20:901.

*Primary Examiner*—Henry R. Jiles
*Assistant Examiner*—J. G. Mullins

[57] ABSTRACT

The invention features compounds having anti-arthritic activity and having the formula

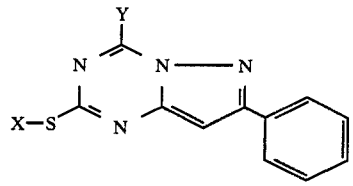

wherein X is an alkyl group having between 1 and 8, inclusive, carbon atoms and Y is a hydroxyalkylamino group having between 2 and 8, inclusive, carbon atoms; a dialkylamino group having between 2 and 12, inclusive, carbon atoms; a carboxyalkylamino group having between 2 and 9, inclusive, carbon atoms; a heterocycloalkyl group having between 2 and 5, inclusive, carbon atoms and having nitrogen as a hetero atom; an alkylthioalkylamino group having between 3 and 10, inclusive, carbon atoms; or a heteroarylalkylthioalkylamino group having between 5 and 14, inclusive, carbon atoms and having ntrogen as a hetero atom.

The invention further features compounds having similar activity and having the formula

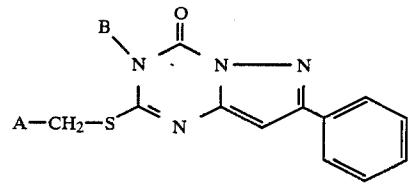

wherein A is H, an alkyl group having between 1 and 8, inclusive, carbon atoms, an aralkyl group having between 6 and 14 inclusive, carbon atoms, an aryl group having between 5 and 14, inclusive, carbon atoms, or a heteroaryl grour having between 3 and 12, inclusive, carbon atoms and having nitrogen as a hetero atom; and B is H, benzyl, a carboalkoxy group having between 2 and 8, inclusive, carbon atoms, or an allyl group having between 3 and 8, inclusive, carbon atoms.

The invention additionally features compounds having similar activity and having the formula

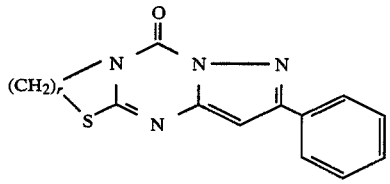

wherein r is an integer between 2 and 4, inclusive.

10 Claims, No Drawings

ANTI-INFLAMMATORY AND ANTI-ARTHRITIC PYRAZOLO-[1,5-a]-1,3,5-TRIAZINE DERIVATIVES, COMPOSITIONS, AND METHOD OF USE THEREFOR

This application is a continuation in part of Kim, U.S. Ser. No. 741,819, filed June 6,1985, now abandoned.

BACKGROUND OF THE INVENTION

This invention relates to non-steroidal anti-inflammatory agents, such as are useful for the treatment of arthritis.

SUMMARY OF THE INVENTION

In general, the invention features in one aspect compounds having the general formula

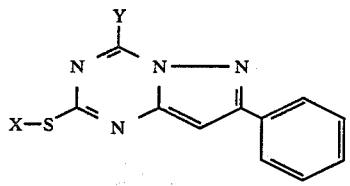

(1)

wherein X is an alkyl group (e.g., methyl) having between 1 and 8, inclusive, carbon atoms and Y is a hydroxyalkylamino group (e.g., ethanolamino) having between 2 and 8, inclusive, carbon atoms; a dialkylamino group (e.g., dimethylamino) having between 2 and 12, inclusive, carbon atoms; a carboxyalkylamino group having between 2 and 9, inclusive, carbon atoms; a heterocycloalkyl group (e.g., thiazolidinyl) having between 2 and 5, inclusive, carbon atoms and having nitrogen as a hetero atom; an alkylthioalkylamino group (e.g., ethylthioethylamino) having between 3 and 10, inclusive, carbon atoms; or a heteroarylalkylthioalkylamino group (e.g., 2-pyridylmethyl thioethylamino) having between 5 and 14, inclusive, carbon atoms and having nitrogen as a hetero atom. Preferably, all alkyl and allyl groups contain between 1 and 4, inclusive, carbon atoms, and all aryl groups contain a single phenyl ring.

Preferred embodiments include: 4-carboxymethylamino-2-methylthio-7-phenylpyrazolo [1,5-a]-1,3,5-triazine; 4-[(3 methylthio-1-carboxy)]propylamino-2-methylthio-7- phenylpyrazolo [1,5-a]-1,3,5-triazine; 2-methylthio-7-phenyl-4-[2-(2-pyridyl) methylthio]ethylamino]-pyrazolo [1,5-a]-1,3,5-triazine; 4-dimethylamino-2-methylthio-7-phenylpyrazolo [1,5-a]-1,3,5-triazine; 4-(2-ethanol)amino-2-methylthio-7-phenylpyrazolo [1,5-a]-1,3,5-triazine; 4-thiazolidinyl-2-methylthio-7-phenylpyrazolo [1,5-a]-1,3,5-triazine; or pharmaceutically acceptable salts thereof.

In another aspect the invention features compounds having the general formula

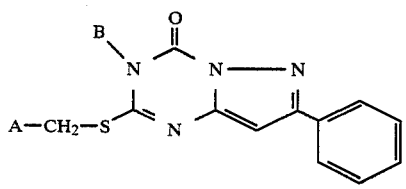

(2)

wherein A is H, an alkyl group having between 1 and 8, inclusive, carbon atoms, an aralkyl group (e.g., benzyl) having between 6 and 14, inclusive, carbon atoms, an aryl group (e.g., phenyl) having between 5 and 14, inclusive, carbon atoms, or a heteroaryl group (e.g., pyridine) having between 3 and 12, inclusive, carbon atoms and having nitrogen as a hetero atom; and B is H, benzyl, a carboalkoxy group having between 2 and 8, inclusive, carbon atoms, an alkyl group having between 1 and 8, inclusive, carbon atoms, or an allyl group having between 3 and 8, inclusive, carbon atoms. Preferably, all allylic and alkyl groups contain between 1 and 4, inclusive, carbon atoms, and all aryl groups contain one or two rings.

Preferred embodiments of the invention include: 3-benzyl-2-methylthio-7-phenylpyrazolo [1,5-a]-1,3, 5-triazine-4-one; 3 carbethoxymethyl-2-methylthio-7-phenyl pyrazolo [1,5-a]-1,3,5-triazine-4-one; 2-(2- pyridylmethyl)thio-7-phenylpyrazolo [1,5-a]-1,3, 5-triazine-4-one; 2-(3-pyridylmethyl) thio-7-phenylpyrazolo [1,5-a]-1,3,5-triazine-4-one; 2-(4-pyridylmethyl) thio-7-phenylpyrazolo [1,5-a]-1,3,5-triazine-4-one; 2-benzylthio-7-phenylpyrazolo [1,5-a]-1,3,5-triazine4-one; 2-(4-imidazolylmethylthio)-7-phenylpyrazolo [1,5-a]-1,3,5-triazine-4-one; 2-(2-benzimidazolylmethylthio)-7-phenylpyrazolo [1,5-a]-1,3,5-triazine-4-one; or pharmaceutically acceptable salts thereof.

The invention features, in another aspect, a compound having the formula

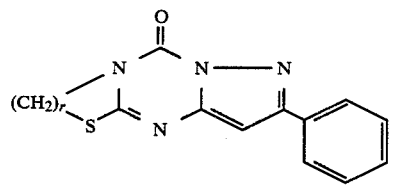

(3)

wherein r is an integer between 2 and 4, inclusive.

Preferred embodiments of the invention include 8-phenyl-dihydrothiazolo [2', 3'-d]-pyrazolo [1,5-a]-1,3,5-triazine-6-one, or a pharmacentically acceptable salt thereof.

In addition to anti-arthritic activity, when a therapeutically effective amount of the compound is administered in a pharmaceutically acceptable carrier, e.g., magnesium carbonate or lactose, the compounds have antiulcer activity against ulcers induced by dimaprit and indomethacin, and can provide anti-inflammatory action without gastric irritation.

When injected or administered in the form of a pill, tablet, capsule, or liquid, the compounds are non-toxic, non-mutagenic, stable and will pass through the stomach without losing their effectiveness.

Other features and advantages will be apparent from the following description of the preferred embodiments, and from the claims.

DESCRIPTION OF THE PREFERRED EMBODIMENTS

Structure

The compounds of the invention have the general formula (1), (2), or (3). Examples of preferred compounds are those referred to as preferred embodiments above.

The compounds are derivatives of 7-phenylpyrazolo [1,5-a]-1,3,5-triazine having a nitrogen at the ring junction. All the compounds can exhibit tautomerism, and the formulas are intended to cover all tautomers.

The compounds or pharmaceutically acceptable salts thereof can be administered alone or in combination with a pharmaceutically acceptable carrier or diluent.

Acceptable salts include hydrochlorides, hydrobromides, and sulfates. Particularly useful organic acid salts are citrates, acetates, maleates, and fumarates.

For oral administration the pharmaceutical composition can most conveniently be in the form of capsules or tablets, which may be slow release tablets. The composition can also be in the form of a dragee or syrup.

Synthesis

The compounds of formula (1) can be synthesized as follows.

The starting material is an amine of formula (4), (5), (6), (7), or (8):

$$\begin{array}{c} R^2 \\ \diagdown \\ NH \\ \diagup \\ R^3 \end{array} \quad (4)$$

where $R^2$ and $R^3$ are the same or different lower ($C_1$–$C_4$) alkyl groups;

$$HO(CH_2)_nNH_2 \quad (5)$$

wherein n is equal to 2–6, inclusive;

$$\begin{array}{c} R \\ | \\ H_2N-CH-CO_2H \end{array} \quad (6)$$

wherein R is H, or the identifying group of the L or D form of an amino acid;

(7) [thiazolidine structure with NH and S]

(8) $NH_2-CH_2CH_2SCH_2-$[pyridyl]

The amine undergoes a condensation reaction with a reagent such as (9) [pyrazolo-triazine structure with E leaving group and phenyl]

where E is a good leaving group, e.g., a halogen (e.g., Cl or Br), or alkoxy (e.g., methoxy or ethoxy). X in formula (9) is as defined above for formula (1).

The condensation reaction is preferably carried out in an inert protic solvent, e.g., water, alcohol, ethoxyethanol, tetrahydrofuran, acetonitrile, dimethyformamide, or a mixture of these solvents at room temperature. If necessary, a base such as KOH, NaOH, $K_2CO_3$, $NaHCO_3$, or triethylamine can be used as an acid scavenger.

Compounds within formula (9) can be synthesized according to known methods, e.g., Capuno et al., Chem. Ber. 104, 3039 (1974); J. Kobe et al., J. Het. Chem., 11, 199 (1974); K. Senga et al., J. Het. Chem., 12, 893 (1973) and J. Med. Chem., 25, 243 (1982). The amine compounds within formulas (4), (5), (6), (7) and (8) are commercially available or can be synthesized according to standard methods, e.g., G. J. Durant et al., J. Med. Chem., 20, 901 (1977).

Specific compounds are made as follows.

4-[(3-methylthio-1-carboxy)]propylamino-2-methylthio-7-phenylpyrazolo [1,5-a]-1,3,5-triazine 1.2 ml 1N-NaOMe is added to a suspension of L-methionine (150 mg) in 5 ml methanol, followed by 290 mg of 4-methoxy-2-methylthio-7-phenylpyrazolo [1, 5-a]-1, 3, 5-triazine and the mixture is stirred at room temperature for 1 hr. After evaporation of solvent in vacuo, the residue is partitioned between water and $CHCl_3$. The aqueous layer is acidified with 1N-HCl to precipitate 300 mg of a pale yellow solid. The solid is collected by filtration, washed with water, and then dried. m.p. 225° C. (decomposes). TLC (silica gel: $CHCl_3$/MeOH=3:1)R f=0.39. Anal. cal'cd for $C_{17}H_{19}N_5O_2S_2$: C, 52.41; H, 4.91; N, 17.98. Found: C, 51.97; H, 4.80; N, 17.91

2-methylthio-7-phenyl-4-[2-[(2-pyridyl) methylthio]ethylamino]-pyrazolo [1,5-a]-1,3,5-triazine 4 ml 1N-NaOMe is added to to a suspension of 270 mg of 4-methoxy-2-methylthio-7-phenylpyrazolo [1,5-a]-1,3, 5-triazine and 520 mg of 2-pyridylmethylthioethylamine dihydrobromide in 10 ml MeOH. After stirring at room temperature for 1 hr., the solvent is evaporated in vacuo, and the residue is partitioned between water and chloroform. The chloroform layer is washed with water several times, then dried over $MgSO_4$. After the removal of solvent, the residue is purified by chromatographing on silica gel (30 g) using chloroform, followed by chloroform-acetone (19:1) as eluants. Appropriate fractions are collected, and the solvent removed to give 280 mg of a pale yellow solid. m.p. 119°–120° C. TLC (silica gel: $CHCl_3$/acetone=9:1)$R_f$=0.42. Anal. cal'cd. for $C_{20}H_{20}N_6S_2$ (0.4 $H_2O$): C, 58.15; H, 5.00; N, 20.34. Found: C, 57.97, H, 4.89; N, 20.03.

4-Carboxymethylamino-2-methylthio-7-phenylpyrazolo [1-5-a]-1,3,5-triazine;
4-(2-ethanol)amino-2-methylthio-7-phenylpyrazolo[1,5-a]-1,3,5,-triazine;
4-thiazolidinyl-2-methylthio-7-phenylpyrazolo [1,5-a]-1,3,5-triazine and
4-dimethylamino-2-methylthio-7-phenylpyrazolo [1,5-a]-1,3,5-triazine are prepared in analogous fashion by making appropriate modifications of the above-described procedures.

The compounds of formula (2) can be synthesized as follows. A compound of formula (10)

(10) [structure with HN-C(=O), S, NH, and phenyl groups]

is condensed with an alkylating agent, e.g., alkyl halide (e.g., methyl iodide), dialkyl sulfate (e.g., dimethylsulfate), aralkyl halide (e.g., benzyl chloride), or heteroaralkyl halide (e.g., 2, 3, or 4-(picolyl) chloride hydrochloride). If desired, the initial condensation product is further condensed with an allyl halide (e.g., allyl chloride), aralkyl halide (e.g., benzyl chloride), or

Z-CH$_2$-COOR′(11)

wherein Z is a halogen and R′ is an alkyl group (e.g., methyl). All condensation reactions are preferably carried out in the presence of base (e.g., NaOH, Na$_2$CO$_3$) in an inert protic solvent described previously.

The above-described alkylating agents are commercially available.

Specific compounds are made as follows.

2-(2-pyridylmethyl)thio-7-phenylpyrazolo [1,5-a]-1,3,5-triazine-4-one 3 ml 2N-NaOH is added to a suspension of 490 mg of 7-phenyl-2-thiopyrazolo [1,5-a]-1,3,5-triazine-4-one in 10 ml ethanol. After a clear solution is obtained, a solution of 330 mg of 2-picolyl chloride hydrochloride in 2 ml ethanol is added and the mixture is stirred at room temperature for 1 hr. The mixture is acidified with acetic acid (pH 4) and the resulting colorless precipitate is collected by filtration. The precipitate is washed sequentially with water, ethanol, and ether, then dried to yield 590 mg of a colorless solid. m.p. 233°–234° C. (decomposition). TLC (silica gel: CHCl$_3$/MeOH=9:1)R$_f$=0.47. Anal. cal'cd for C$_{17}$H$_{13}$N$_5$OS: C, 60.87; H, 3.90; N, 20.88. Found: C, 61.02; H, 3.86; N, 20.89.

3-Carbethoxymethyl-2-methylthio-7-phenylpyrazolo [1,5-a]-1,3,5-triazine-4-one

A mixture of 260 mg of 2-methylthio-7-phenylpyrazolo [1,5-a]-1,3,5-triazine-4-one and 140 mg of anhydrous potassium carbonate in 5 ml dry dimethylformamide is stirred at room temperature for 15 min while 0.14 ml ethylbromacetate is added dropwise. The mixture is stirred at room temperature overnight, filtered, and the filter cake washed with dimethylformamide.

After evaporation of solvent in vacuo, the residue is partitioned between water and chloroform. The chloroform layer is washed with water, then dried over MgSO$_4$. The solvent is evaporated in vacuo to dryness. Recrystallization of the residue from ethanol yields 170 mg of needle-like crystals with a melting range of 173°–174° C. Mass spectral analysis shows a molecular ion of M/e 344.

2-(3Pyridylmethyl)thio-7-phenylpyrazolo [1,5-a]-1,3,5-triazine-4-one; 2-(4-pyridylmethyl)thio-7-phenylpyrazolo [1,5-a]-1,3,5-triazine-4-one; 2-benzylthio-7-phenylpyrazolo [1,5-a]-1,3,5-triazine-4-one; 3-benzyl-2-methylthio-7-phenyl pyrazolo [1,5-a]-1,3,5-triazine-4-one 2-(2-enzimidazolyl methylthio)-7-phenylpyrazolo [1,5-a]-1,3,5-triazine-4-one; and 2-(4-imidazolylmethylthio)-7-phenylpyrazolo [1,5-a]-1,3,5-triazine-4-one are prepared in analogous fashion by making appropriate modifications of the above-described procedures.

The compounds of formula (3) can be synthesized by condensing a compound of formula (10) with a dialkylating agent, e.g., 1,2-dibromopropane. Accordingly, 8-phenyl-dihydrothiazolo [2′,3′-d]-pyrazolo [1,5-a]-1,3,5-triazine-6-one is prepared by treating 7-phenyl-2-thiopyrazolo [1,5-a]-1,3,5-triazine-4-one in ethanol with sodium hydride, under standard conditions; 1,2-dibromopropane is added and the reaction is stirred overnight. The product is obtained by standard workup of the reaction mixture.

Use

When administered to mammals alone or together with a pharmaceutically acceptable carrier substance (e.g., orally, topically, intravenously, parenterally, nasally, or by suppository), the compounds of the invention are useful for the treatment of arthritis. The compounds of the invention can also be used to prevent peptic and gastric ulcers, and to treat reflux esophagitis, acute erosive gastritis, and pancreatic insufficiency.

The compounds of the invention inhibit ulcers induced by non-steroidal anti-inflammatory drugs, e.g., aspirin and indomethacin, without inhibiting their anti-inflammatory and analgesic activity. Thus, the compounds can be particularly useful in treating or preventing gastric ulcers in patients, e.g., arthritics, who consume non-steroidal anti-inflammatory drugs. The anti-inflammatory action of the compounds can even reduce or eliminate the dosage required of non-steroidal anti-inflammatory drugs.

The compounds can be administered to a mammal in a dosage of 5 to 100 mg/kg/day, preferably 10 to 50 mg/kg/day.

Other embodiments are within the following claims.

I claim:

1. A compound having the formula

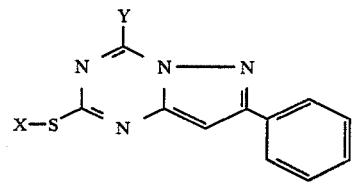

wherein X is an alkyl group having between 1 and 8, inclusive, carbon atoms and Y is a hydroxyalkylamino group having between 2 and 8, inclusive, carbon atoms; a dialkylamino group having between 2 and 12, inclusive, carbon atoms; a carboxyalkylamino group having between 2 and 9, inclusive, carbon atoms; alkylthioalkylamino group having between 3 and 10, inclusive, carbon atoms; a thiazolidinyl group or a pyridylmethylthioethylamino group.

2. The compound of claim 1, wherein X is —CH$_3$; and Y is —NHCH$_2$CO$_2$H;

said compound having the name 4-carboxymethylamino-2-methylthio-7-phenylpyrazolo [1,5-a]1,3,5-triazine;

or a pharmaceutically acceptable salt thereof.

3. The compound of claim 1, wherein X is —CH$_3$; and Y is:

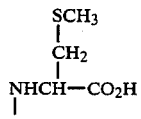

said compound having the name 4-[(3-methylthio-1-carboxy)]propylamino-2-methylthio-7-phenylpyrazolo [1,5-a]-1,3,5-triazine;

or a pharmaceutically acceptable salt thereof.

4. The compound of claim 1, wherein X is —CH₃; and Y is:

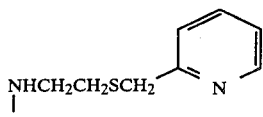

said compound having the name 2-methylthio-7-phenyl-4-[2-(2-pyridyl) methylthio]ethylaminopyrazolo [1,5-a ]-1,3,5-triazine;

or a pharmaceutically acceptable salt thereof.

5. The compound of claim 1, wherein X is —CH₃; and Y is —NHCH₂CH₂OH;

said compound having the name 4-(2-ethanol)amino-2-methylthio-7-phenylpyrazolo [1,5-a]-1,3,5-triazine;

or a pharmaceutically acceptable salt thereof.

6. The compound of claim 1, wherein X is —CH₃; and Y is N(CH₃)₂;

said compound having the name 4-dimethylamino-2-methylthio-7-phenylpyrazolo[1,5-a]-1,3,5-triazine;

or a pharmaceutically acceptable salt thereof.

7. The compound of claim 1, wherein X is —CH₃; and Y is

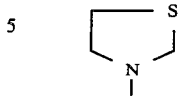

said compound having the name 4-thiazolidinyl-2-methylthio-7-phenylpyrazolo [1,5-a]-1,3,5-triazine;

or a pharmaceutically acceptable salt thereof.

8. A therapeutic composition for preventing or treating inflammation and arthritis comprising an anti-inflammatory effective amount of the compound of claim 1 together with a pharmaceutically acceptable carrier substance.

9. The therapeutic composition of claim 8 wherein said composition is in the form of a pill, tablet, capsule, or liquid for oral administration to a human patient in need of said compound.

10. A method of treating or preventing inflammation and arthritis in a mammal comprising administering to said mammal an anti-inflammatory effective amount of the compound of claim 1.

* * * * *